US012635902B2

(12) United States Patent
Chandel et al.

(10) Patent No.: US 12,635,902 B2
(45) Date of Patent: May 26, 2026

(54) METHOD AND SYSTEM FOR BREATHING ANALYSIS USING A PERSONAL DIGITAL ASSISTANT (PDA)

(71) Applicant: Tata Consultancy Services Limited, Mumbai (IN)

(72) Inventors: Vivek Chandel, Gurgaon (IN); Avik Ghose, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 756 days.

(21) Appl. No.: 17/970,739

(22) Filed: Oct. 21, 2022

(65) Prior Publication Data

US 2023/0148898 A1     May 18, 2023

(30) Foreign Application Priority Data

Nov. 17, 2021    (IN) .............................. 202121052814

(51) Int. Cl.
*A61B 5/08* (2006.01)
*A61B 5/00* (2006.01)

(52) U.S. Cl.
CPC .......... *A61B 5/0816* (2013.01); *A61B 5/6823* (2013.01); *A61B 5/7264* (2013.01); *A61B 5/7278* (2013.01); *A61B 2562/0219* (2013.01)

(58) Field of Classification Search
None
See application file for complete search history.

(56) References Cited

U.S. PATENT DOCUMENTS

2018/0256074 A1*   9/2018  Persidsky .............. A61B 5/113

OTHER PUBLICATIONS

Arthittayapiwat et al., "Chest Experimentation Measurement in 3-Dimension by Using Accelerometers," Engineering Journal, 23(2) (2019).
Belsare et al., "Computation of Cigarette Smoke Exposure Metrics from Breathing," IEEE Trans Biomed Eng., 67(8):2309-2316 (2020).
Karacocuk et al., "Inertial Sensor-Based Respiration Analysis," IEEE Transactions on Instrumentation and Measurement, 68(11) (2019).

(Continued)

*Primary Examiner* — Aurelie H Tu
(74) *Attorney, Agent, or Firm* — Finnegan, Henderson, Farabow, Garrett & Dunner, LLP

(57) ABSTRACT
This disclosure relates generally to breathing analysis of a subject. Breathing analysis on a regular basis allows early detection for the onset of diseases, thus saving resources and cost in treatments. The existing state of art techniques require specialized devices to collect-infer the breathing and are mostly limited to analyzing breathing rate. The disclosure enables breathing analysis using a personal digital assistant (PDA). The breathing analysis includes (a) estimating exhale period-inhale period, (b) estimating the breathing rate and (c) determining the type of breathing. A PDA such as a smartphone is used receive accelerometer data from a subject. The received data is pre-processed in several steps including estimating a plurality of parameters, identifying a plurality of breathing cycles. The breathing cycles of the subject are further analyzed at real time based on the plurality of parameters to provide the breathing analysis of a subject.

3 Claims, 10 Drawing Sheets

(56) References Cited

OTHER PUBLICATIONS

Sardini et al., "Instrumented Wearable Belt for Wireless Health Monitoring," Procedia Engineering, 5:580-583 (2010).
Tadi et al., "Accelerometer-Based Method for Extracting Respiratory and Cardiac Gating Information for Dual Gating during Nuclear Medicine Imaging," International Journal of Biomedical Imaging (2014).

* cited by examiner

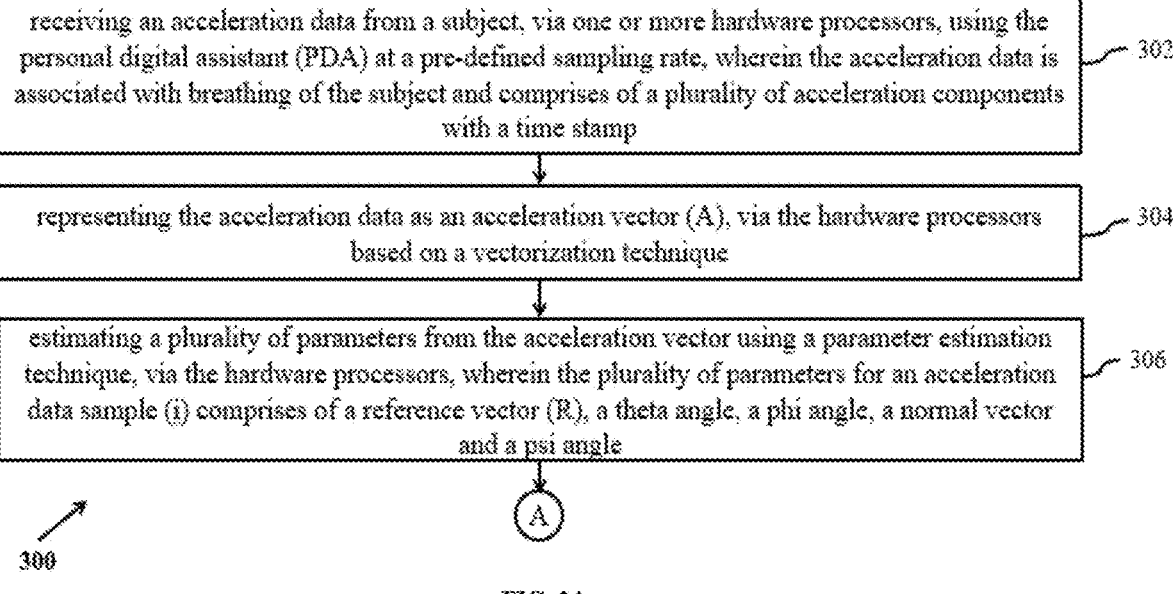

receiving an acceleration data from a subject, via one or more hardware processors, using the personal digital assistant (PDA) at a pre-defined sampling rate, wherein the acceleration data is associated with breathing of the subject and comprises of a plurality of acceleration components with a time stamp ⌐ 302 representing the acceleration data as an acceleration vector (A), via the hardware processors based on a vectorization technique ⌐ 304 estimating a plurality of parameters from the acceleration vector using a parameter estimation technique, via the hardware processors, wherein the plurality of parameters for an acceleration data sample (i) comprises of a reference vector (R), a theta angle, a phi angle, a normal vector and a psi angle ⌐ 306

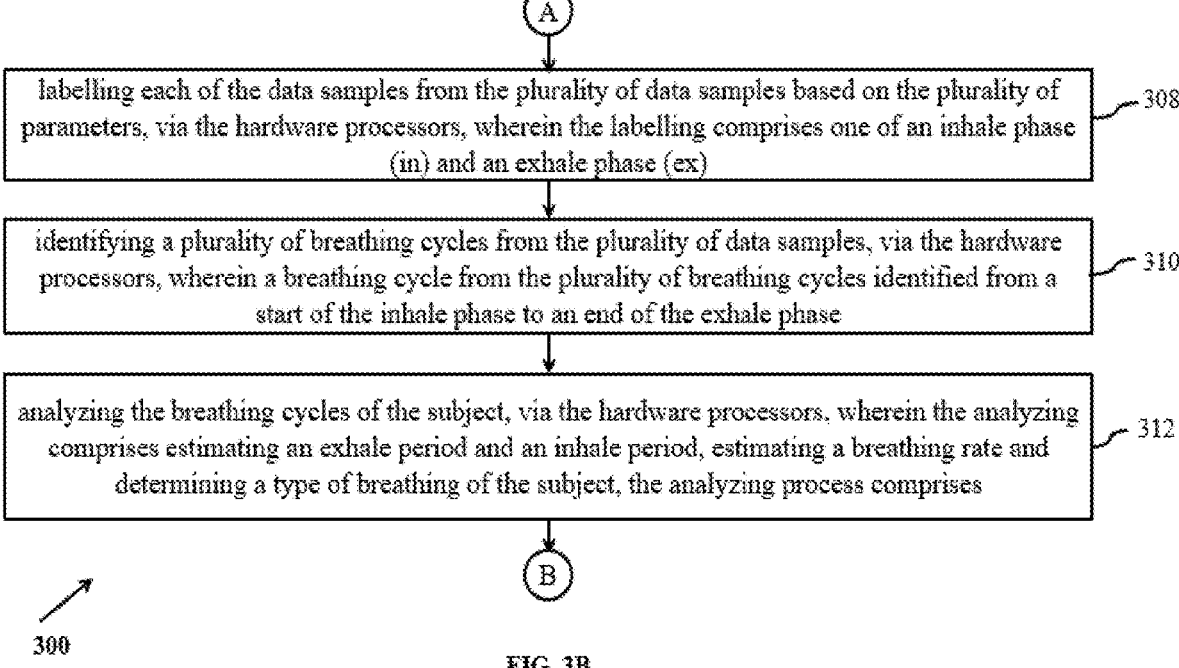

labelling each of the data samples from the plurality of data samples based on the plurality of parameters, via the hardware processors, wherein the labelling comprises one of an inhale phase (in) and an exhale phase (ex) — 308 identifying a plurality of breathing cycles from the plurality of data samples, via the hardware processors, wherein a breathing cycle from the plurality of breathing cycles identified from a start of the inhale phase to an end of the exhale phase — 310 analyzing the breathing cycles of the subject, via the hardware processors, wherein the analyzing comprises estimating an exhale period and an inhale period, estimating a breathing rate and determining a type of breathing of the subject, the analyzing process comprises — 312

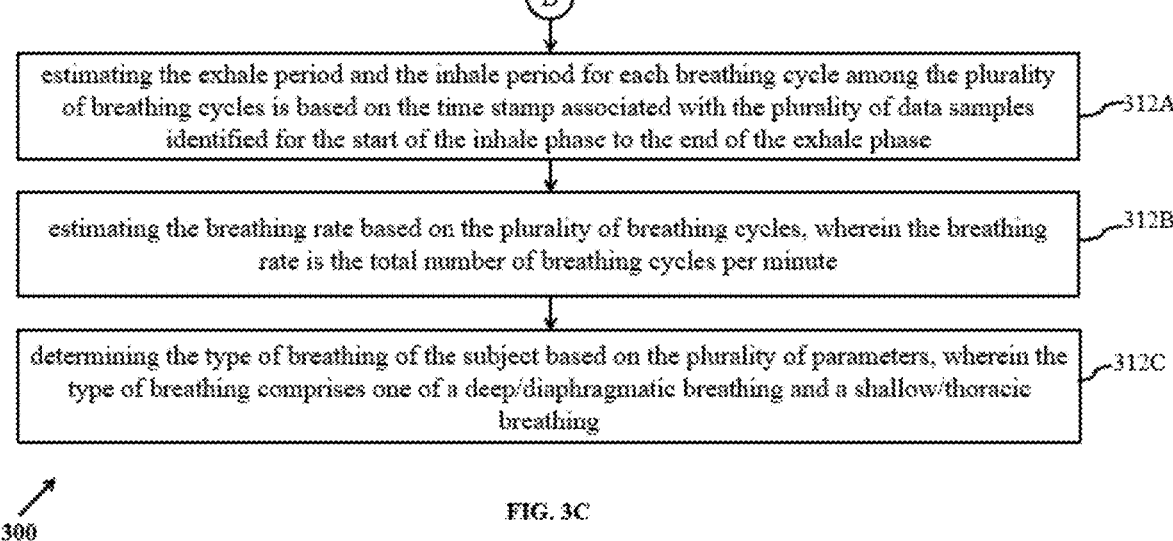

estimating the exhale period and the inhale period for each breathing cycle among the plurality of breathing cycles is based on the time stamp associated with the plurality of data samples identified for the start of the inhale phase to the end of the exhale phase ⌐312A estimating the breathing rate based on the plurality of breathing cycles, wherein the breathing rate is the total number of breathing cycles per minute ⌐312B determining the type of breathing of the subject based on the plurality of parameters, wherein the type of breathing comprises one of a deep/diaphragmatic breathing and a shallow/thoracic breathing ⌐312C

METHOD AND SYSTEM FOR BREATHING ANALYSIS USING A PERSONAL DIGITAL ASSISTANT (PDA)

PRIORITY CLAIM

This U.S. patent application claims priority under 35 U.S.C. § 119 to: India application No. 202121052814, filed on Nov. 17, 2021. The entire contents of the aforementioned application are incorporated herein by reference.

TECHNICAL FIELD

The disclosure herein generally relates to field of breathing analysis, and, more particularly, to a method and a system for breathing analysis using a personal digital assistant (PDA).

BACKGROUND

Breathing analysis on a regular basis allows screening for the onset of diseases. Early detection of diseases saves resources and cost in treatments. Breathing analysis has many applications and is community-deployable, can be used at point-of-care, and is completely non-invasive way of identifying and controlling many potential health concerns. The breathing analysis has the potential to be deployed much more widely in the community due to its non-invasive nature.

A detailed analysis of breathing requires accurate signals representative of the inhale and the exhale stages for every breathing cycle. For the extraction of the details of inhale and the exhale, a chest wearable, or the technique of impedance pneumography is utilized to indirectly infer the respiration signal. To infer the respiration signal, the existing state of art techniques requires a specialized setup/hardware and cannot be ubiquitously used to conveniently monitor the respiration vitals except in clinical set-ups/hospitals.

Hence the existing state of art techniques mostly require specialized devices to collect and infer the breathing signal. Further few other existing state of art techniques utilize portable solutions/personal digital assistants such as mobile phones but breathing analysis is limited to calculating only a breathing rate. However, for accurate analysis and to derive true insights from breath monitoring, analysis of only breathing rate is not sufficient.

SUMMARY

Embodiments of the present disclosure present technological improvements as solutions to one or more of the above-mentioned technical problems recognized by the inventors in conventional systems. For example, in one embodiment, a system for breathing analysis using a personal digital assistant (PDA) is provided. The system includes a memory storing instructions, one or more communication interfaces, and one or more hardware processors coupled to the memory via the one or more communication interfaces, wherein the one or more hardware processors are configured by the instructions to receive an acceleration data from a subject, via one or more hardware processors, using the personal digital assistant at a pre-defined sampling rate, wherein the acceleration data is associated with breathing of the subject and the acceleration data comprises a plurality of data samples with a time stamp. The system is further configured to represent the acceleration data as an acceleration vector (A), via the hardware processors, based on a vectorization technique. The system is further configured to estimate a plurality of parameters from the acceleration vector using a parameter estimation technique, via the hardware processors, wherein the plurality of parameters for an acceleration data sample comprises of a reference vector (R), a theta angle, a phi angle, a normal vector and a psi angle. The system is further configured to label each of the data samples from the plurality of data samples based on the plurality of parameters, via the hardware processors, wherein the labelling comprises one of an inhale phase (in) and an exhale phase (ex). The system is further configured to identify a plurality of breathing cycles from the plurality of data samples, via the hardware processors, wherein a breathing cycle from the plurality of breathing cycles identified from a start of the inhale phase to an end of the exhale phase. The system is further configured to analyze the breathing cycles of the subject, via the hardware processors, wherein the analyzing comprises estimating an exhale period and an inhale period, estimating a breathing rate and determining a type of breathing of the subject, for the analyzing process the one or more hardware processors are configured by the instructions to: estimate the exhale period and the inhale period for each breathing cycle among the plurality of breathing cycles is based on the time stamp associated with the plurality of data samples identified for the start of the inhale phase to the end of the exhale phase, estimate the breathing rate based on the plurality of breathing cycles, wherein the breathing rate is the total number of breathing cycles per minute; and determine the type of breathing of the subject based on the plurality of parameters, wherein the type of breathing comprises one of a deep/diaphragmatic breathing and a shallow/thoracic breathing.

In another aspect, a method for breathing analysis using a personal digital assistant (PDA) is provided. The method includes receiving an acceleration data from a subject using the personal digital assistant (PDA) at a pre-defined sampling rate, wherein the acceleration data is associated with breathing of the subject and the acceleration data comprises of a plurality of data samples with a time stamp. The method further includes representing the acceleration data as an acceleration vector (A) based on a vectorization technique. The method further includes estimating a plurality of parameters from the acceleration vector using a parameter estimation technique, wherein the plurality of parameters for an acceleration data sample comprises of a reference vector, a theta angle, a phi angle, a normal vector and a psi angle. The method further includes labelling each of the data samples from the plurality of data samples based on the plurality of parameters, wherein the labelling comprises one of an inhale phase (in) and an exhale phase (ex). The method further includes identifying a plurality of breathing cycles from the plurality of data samples, wherein a breathing cycle from the plurality of breathing cycles identified from a start of the inhale phase to an end of the exhale phase. The method further includes analyzing the breathing cycles of the subject, wherein the analyzing comprises estimating an exhale period and an inhale period, estimating a breathing rate and determining a type of breathing of the subject, the analyzing process comprises: estimating the exhale period and the inhale period for each breathing cycle among the plurality of breathing cycles is based on the time stamp associated with the plurality of data samples identified for the start of the inhale phase to the end of the exhale phase, estimating the breathing rate based on the plurality of breathing cycles, wherein the breathing rate is the total number of breathing cycles per minute; and determining the type of breathing of the subject based on the plurality of parameters, wherein the type of breathing comprises one of a deep/diaphragmatic breathing and a shallow/thoracic breathing.

In yet another aspect, there are provided one or more non-transitory machine-readable information storage mediums comprising one or more instructions, which when executed by one or more hardware processors causes a method for breathing analysis using a personal digital assistant (PDA). The method includes receiving an acceleration data from a subject using the personal digital assistant (PDA) at a pre-defined sampling rate, wherein the acceleration data is associated with breathing of the subject and the acceleration data comprises of a plurality of data samples with a time stamp. The method further includes representing the acceleration data as an acceleration vector (A) based on a vectorization technique. The method further includes estimating a plurality of parameters from the acceleration vector using a parameter estimation technique, wherein the plurality of parameters for an acceleration data sample comprises of a reference vector, a theta angle, a phi angle, a normal vector and a psi angle. The method further includes labelling each of the data samples from the plurality of data samples based on the plurality of parameters, wherein the labelling comprises one of an inhale phase (in) and an exhale phase (ex). The method further includes identifying a plurality of breathing cycles from the plurality of data samples, wherein a breathing cycle from the plurality of breathing cycles identified from a start of the inhale phase to an end of the exhale phase. The method further includes analyzing the breathing cycles of the subject, wherein the analyzing comprises estimating an exhale period and an inhale period, estimating a breathing rate and determining a type of breathing of the subject, the analyzing process comprises: estimating the exhale period and the inhale period for each breathing cycle among the plurality of breathing cycles is based on the time stamp associated with the plurality of data samples identified for the start of the inhale phase to the end of the exhale phase, estimating the breathing rate based on the plurality of breathing cycles, wherein the breathing rate is the total number of breathing cycles per minute; and determining the type of breathing of the subject based on the plurality of parameters, wherein the type of breathing comprises one of a deep/diaphragmatic breathing and a shallow/thoracic breathing.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3A, FIG. 3B and FIG. 3C is a flow diagram illustrating a method for breathing analysis using the PDA in accordance with some embodiments of the present disclosure.

The FIG. 6A, FIG. 6B

The FIG. 7A, FIG. 7B

Figure 1:
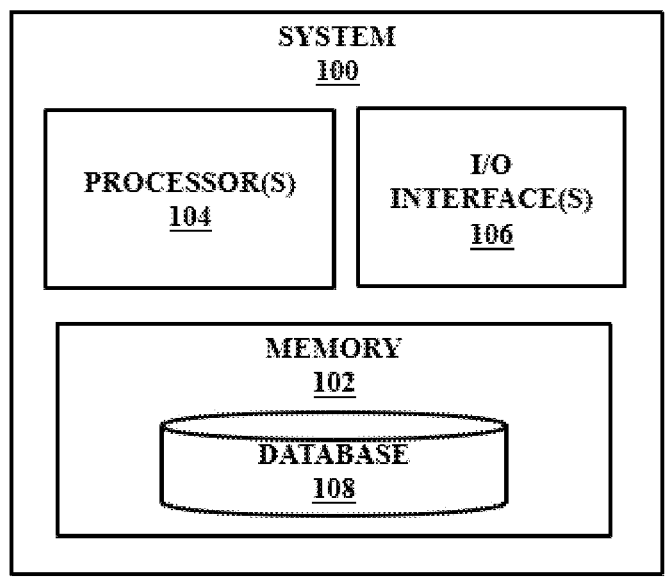
FIG. 1 illustrates an exemplary system for breathing analysis using a personal digital assistant (PDA) according to some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Embodiments herein provide a method and system for breathing analysis using a personal digital assistant (PDA). Breathing analysis on a regular basis allows early detection for the onset of diseases, thus saving resources and cost in treatments. The existing state of art techniques require specialized devices to collect-infer the breathing and are mostly limited to analyzing breathing rate. The disclosure enables breathing analysis using a personal digital assistant (PDA).

Referring now to the drawings, and more particularly to FIG. 1 through FIG. 8C, where similar reference characters denote corresponding features consistently throughout the figures, there are shown preferred embodiments and these embodiments are described in the context of the following exemplary system and/or method.

FIG. 1 is a functional block diagram of a system 100 for breathing analysis using the PDA in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of the system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 is configured to fetch and execute computer-readable instructions stored in the memory 102. The memory 102 further comprises the functional modules of system 100, explained in conjunction with FIG. 2. In an embodiment, the system 100 can be implemented in a variety of computing systems including laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, a touch user interface (TUI) and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) 106 can include one or more ports for connecting a number of devices (nodes) of the system 100 to one another or to another server.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Further, the memory 102 may include a database 108 configured to include information regarding historic data associated the breathing analysis. The memory 102 may comprise information pertaining to input(s)/output(s) of each step performed by the processor(s) 104 of the system 100 and methods of the present disclosure. In an embodiment, the database 108 may be external (not shown) to the system 100 and coupled to the system via the I/O interface 106.

Figure 2:
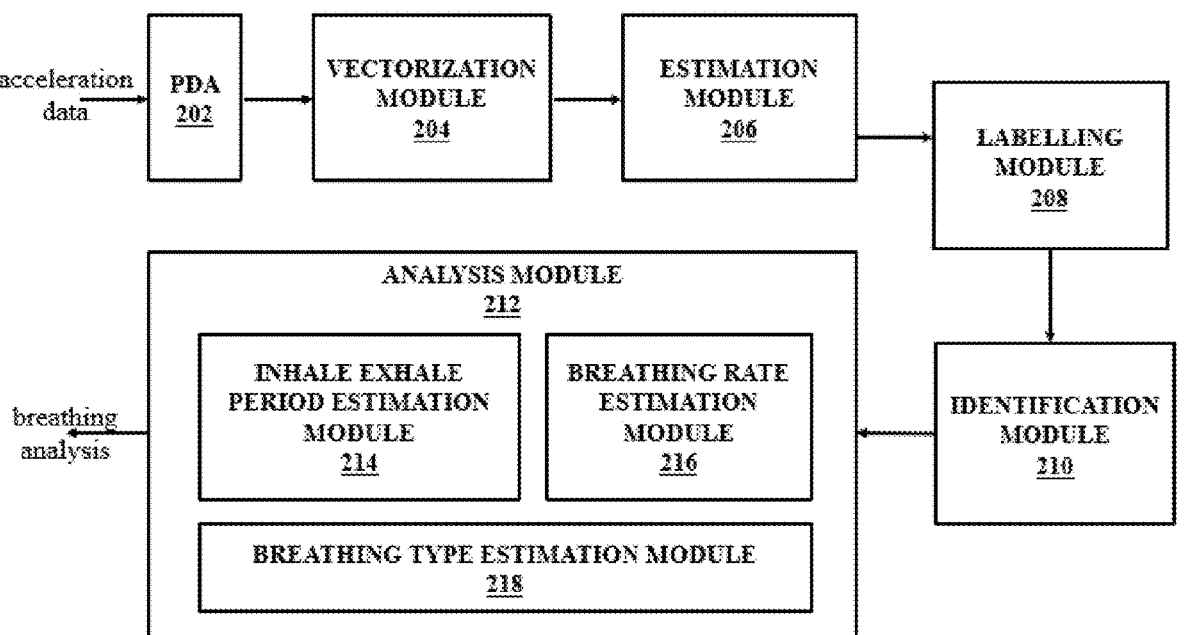
FIG. 2 is a functional block diagram of a system for breathing analysis using the PDA according to some embodiments of the present disclosure.

Functions of the components of system 100 are explained in conjunction with functional overview of the system 100 in FIG. 2 and flow diagram of FIGS. 3A and 3B for breathing analysis using the PDA.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

FIG. 2 is an example functional block diagram of the various modules of the system of FIG. 1, in accordance with some embodiments of the present disclosure. As depicted in the architecture, the FIG. 2 illustrates the functions of the modules of the system 100 that includes breathing analysis using a personal digital assistant (PDA).

The system 100 for breathing analysis using a personal digital assistant (PDA) 202 is configured to receive an acceleration data from a subject, via one or more hardware processors 104, using the personal digital assistant (PDA) 202. The PDA is configured to receive the acceleration data at a pre-defined sampling rate. The acceleration data is associated with breathing of the subject and comprises of a plurality of acceleration components with a time stamp.

In one embodiment, upon receiving the acceleration data at the PDA 202, the acceleration data can be processed for breathing analysis within the PDA 202 using the modules (204 to 212). In another embodiment, the processing of the acceleration data for breathing analysis can run on a separate host system wirelessly using the modules (204 to 212). Further breathing analysis can be displayed in real time on a screen which is available with the separate host system, or in another embodiment, the breathing analysis can be displayed on the PDA 202. Hence the processing of acceleration data for breathing analysis can be performed within the PDA or on a separate system based on a user requirement.

The system 100 further comprises a vectorization module 204 configured for representing the acceleration data as an acceleration vector (A). The acceleration data is represented acceleration vector (A) based on a vectorization technique.

The system 100 further comprises an estimation module 206 configured for estimating a plurality of parameters from the acceleration vector. The plurality of parameters is estimated from the acceleration vector using a parameter estimation technique. The plurality of parameters for an acceleration data sample (i) comprises of a reference vector (R), a theta angle ($\theta_i$), a phi angle ($\varphi_i$), a normal vector ($L_i$) and a psi angle ($\Psi_i$).

The system 100 further comprises a labelling module 208 configured for labelling each of the data samples from the plurality of data samples based on the plurality of parameters. The data samples are labeled as of an inhale phase (in) and an exhale phase (ex).

The system 100 further comprises an identification module 210 configured for identifying a plurality of breathing cycles from the plurality of data samples. A breathing cycle from the plurality of breathing cycles identified from a start of the inhale phase to an end of the exhale phase.

The system 100 further comprises an analysis module 212 configured for analyzing the breathing cycles of the subject. The analyzing comprises (a) estimating an exhale period and an inhale period, (b) estimating a breathing rate and (c) determining a type of breathing of the subject.

The analysis module 212 of the system 200 further comprises an inhale exhale period estimation module 214, a breathing rate estimation module 216 and, a breathing type estimation module 218.

The inhale exhale period estimation module 214 is configured for estimating the exhale period and the inhale period for each breathing cycle among the plurality of breathing cycles is based on the time stamp associated with the plurality of data samples identified for the start of the inhale phase to the end of the exhale phase.

The breathing rate estimation module 216 is configured for estimating the breathing rate based on the plurality of breathing cycles, wherein the breathing rate is the total number of breathing cycles per minute.

The breathing type estimation module 218 is configured for determining the type of breathing of the subject based on the plurality of parameters. The type of breathing comprises one of a deep/diaphragmatic breathing and a shallow/thoracic breathing.

The various modules of the system 100 and the functional blocks in FIG. 2 are configured for breathing analysis using PDA using a set of sensors are implemented as at least one of a logically self-contained part of a software program, a self-contained hardware component, and/or, a self-contained hardware component with a logically self-contained part of a software program embedded into each of the hardware component that when executed perform the a method 300 described using FIG. 3A, FIG. 3B and FIG. 3C, described herein.

Functions of the components of the system in FIG. 2 are explained in conjunction with functional modules of the system 100 stored in the memory 102 and further explained in conjunction with flow diagram of FIG. 3A and FIG. 3B.

The FIG. 3A, FIG. 3B and FIG. 3C with reference to FIG. 1, is an exemplary flow diagram illustrating a method 300 for breathing analysis using a personal digital assistant (PDA) using the system 100 of FIG. 1 according to an embodiment of the present disclosure.

The steps of the method of the present disclosure will now be explained with reference to the components of the system (100) for breathing analysis using a personal digital assistant (PDA) and the modules (202-218) as depicted in FIG. 2 and the flow diagrams as depicted in FIG. 3A, FIG. 3B and FIG. 3C. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 302 of the method (300), an acceleration data is received from a subject using the personal digital assistant (PDA) 202. The acceleration data is received from a subject at a pre-defined sampling rate. The acceleration data is associated with breathing of the subject and the acceleration data comprises of a plurality of data samples with a time stamp.

In an embodiment, the personal digital assistant (PDA) 202 comprises an accelerometer and the PDA 202 has a form factor of a size of a human palm. Further in an example scenario, the PDA 202 comprises a 3-axis accelerometer sensor, and may or may not have an integrated gyroscope, magnetometer or any other sensor. The PDA 202 can play a beep sound and is be equipped with a wireless connectivity means in order to transmit the sensor data to the data processing station-if required.

Figure 4:
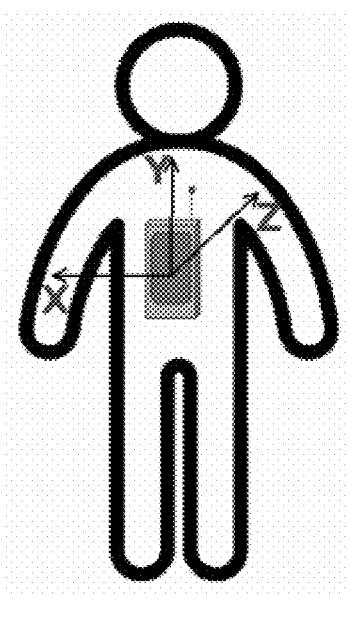
FIG. 4 is a flow diagram illustrating orientation of the PDA with respect to the subject's body for breathing analysis using a personal digital assistant (PDA) in accordance with some embodiments of the present disclosure.

The plurality of acceleration data is received from the PDA 202, with the center of the PDA in contact with a center of torso of the subject, with an upper half of the PDA lying over the chest and a lower half of the PDA lying over a belly of the subject with the top of the PDA directed towards chin of the subject, which is illustrates in the FIG. 4 with the PDA 202 on the subject. Hence the subject is to always face the PDA 202 with the PDA's 202 top directed towards the subject's chin (with the Y-Axis facing upwards).

In an embodiment, the acceleration data is associated with breathing of the subject and is received from the subject at a pre-defined sampling rate. The acceleration data comprises of a plurality of data samples with a time stamp. In an example scenario, the acceleration data is received from the subject at a pre-defined sampling rate of 50 samples per second. A single $i^{th}$ data sample of the acceleration data at t (time stamp) can be represented as shown below:

$$s_i = \{t_i, a_{x(i)}, a_{y(i)}, a_{z(i)}\} \tag{1}$$

where, $a_x$, $a_y$ and $a_z$ represent acceleration in three-axes of the accelerometer at time stamp ($t_i$)

At step 304 of the method (300), the acceleration data is represented as an acceleration vector (A) at the vectorization module 204. The acceleration data is represented as an acceleration vector (A) based on a vectorization technique.

In an embodiment, the vectorization technique includes interpreting each acceleration data sample received from the accelerometer as a vector in 3D with the vector components same as the acceleration value in three dimensions in the data sample expressed in equation 1.

In an embodiment, the acceleration vector (A) is represented as a three-dimensional space (X-axis, Y-axis, and Z-axis) along with the time stamp and is represented:

$$A_i = a_{x(i)}e_1 + a_{y(i)}e_2 + a_{z(i)}e_3 \tag{2}$$

wherein $a_x$, $a_y$ and $a_z$ represent acceleration in three-axes of the accelerometer at time stamp ($t_i$), and $e_1$, $e_2$ and $e_3$ represent unit vectors pointing in X-axis, Y-axis, and Z-axis respectively.

The acceleration vector is a vector representation of the acceleration data and hence retains the plurality of data samples with a time stamp.

At step 306 of the method (300), a plurality of parameters is estimated from the acceleration vector using a parameter estimation technique at the estimation module 206. The plurality of parameters for an acceleration data sample (i) comprises of a reference vector (R), a theta angle ($\theta_i$), a phi angle ($\varphi_i$), a normal vector ($L_i$) and a psi angle ($\Psi_i$).

In an embodiment, the estimation module 206 can be implemented by wirelessly transmitted to another system or can be shared on another device or the process can continue on the system 200.

The reference vector (R) is defined in the Y-axis and the Z-axis rotational plane where the acceleration vector (A) travels. The R is expressed as shown below:

$$R = \frac{\sum_{i=m}^{n} s_i}{n - m + 1} \tag{3}$$

Further the theta angle ($\theta_i$) is an angle between R and A. The theta angle ($\theta_i$) is expressed as shown below:

$$\theta_i = \arccos((R \odot A_i)|((R\|A_i)) \tag{4}$$

where, $\odot$ is an inner product operator for two consecutive vectors

The phi angle ($\varphi_i$) is an angle between the consecutive acceleration vectors. The phi angle ($\varphi_i$) is expressed as shown below:

$$\varphi_i = \theta_i - \theta_{i-1} \tag{5}$$

If n+1=k, then for every sample i>k there is a corresponding $\varphi_i$ 9                                                    10

Further the normal vector ($L_i$) is the vector perpendicular to the plane in which the acceleration vector (A) travels. The normal vector ($L_i$) is expressed as shown below:

$$L_i = R \otimes A_i \qquad (6)$$

where $\otimes$ represents cross product of two consecutive vectors in a 3 dimensional space $\mathbb{R}^3$.

Further a psi angle ($\Psi_i$) is an angle between the $L_i$ and the positive X-axis.

Figure 5A:
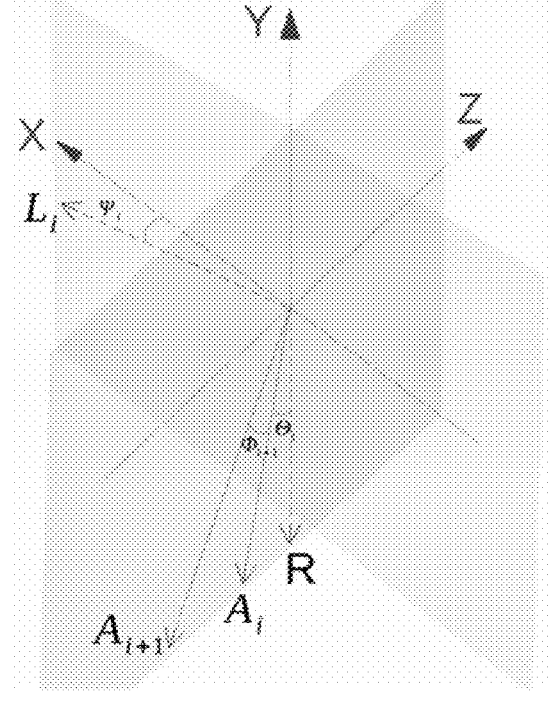
FIG. 5A and FIG. 5B illustrates a plurality of parameters for breathing analysis using the PDA in accordance with some embodiments of the present disclosure.
Figure 5B:
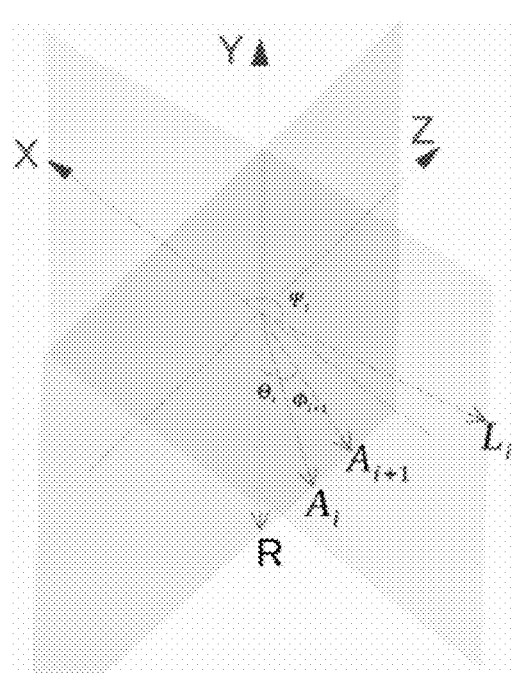

An example scenario has been illustrated in FIG. 5A and FIG. 5B for estimating the plurality of parameters from the acceleration vector. The FIG. 5A represents an example scenario of inhalation for deep breathing, where the vector A travels away from the body of the subject while inhalation owing to the lower half of the PDA 202 moving away from the body of the user. Further FIG. 5B represents a scenario of inhalation for shallow breathing, wherein the vector A travels towards the body of the user while inhalation owing to the lower half of the PDA 202 moving towards body of the subject.

At step 308 of the method (300), each of the data samples from the plurality of data samples is labelled based on the plurality of parameters in the labelling module 208. The labelling of the data samples comprises one of an inhale phase (in) and an exhale phase (ex).

In an embodiment, the data samples are labelled either as the inhale phase (in) or the exhale phase (ex). The labelling is decided based on the plurality of parameters, in an example scenario, the labelling is decided based on the phi angle ($\varphi_i$).

During inhalation, if the phi angle ($\varphi_i$) for every data sample increases, as the acceleration vector ($A_i$) travels farther and farther away from the reference vector R, then a gravity vector right before the first inhalation begins (for samples i<n). Hence, the phi angle ($\varphi_i$).as expressed in (Equation 5) is positive for inhalation, while the phi angle ($\varphi_i$).as expressed in (Equation 5) is negative for exhalation (ex). Therefore, the labelling is identified based on the phi angle ($\varphi_i$) of each of the data samples, where the data sample is labelled as the inhale phase (in) when the phi angle ($\varphi_i$) is positive and data sample is labelled as the exhale phase (ex) when the phi angle ($\varphi_i$) is negative. Hence, the data samples can be labeled as inhalation (in) or exhalation (ex) as follows:

$$\text{Data sample, } i := \text{in if } \varphi_i > 0 \qquad (7)$$

$$:= ex \text{ if } \varphi_i < 0$$

At step 310 of the method (300), a plurality of breathing cycles are identified from the plurality of data samples at the identification module 210. The plurality of breathing cycles identified from a start of the inhale phase to an end of the exhale phase, wherein each breathing cycle begins at the start of the inhale phase and ends at the end of the exhale phase.

In natural breathing, a single inhalation cycle (and exhalation cycle) takes place in a continuous manner, wherein the single cycle of breathing can be defined as the period from the start of an inhale phase to the end of exhale phase. While. Hence a single inhale phase is present as a set of continuous samples labeled as inhale phase or 'in' as per (7). Similarly, a single inhale phase is present as a set of continuous samples labeled as a exhale phase or 'ex'. Further an inhale phase followed by an exhale phase-which constitutes a single breathing cycle ($C_j$). A breathing session or a plurality of breathing cycles can therefore be represented as a set of continuous breathing cycles. A $C_j$ can be represented as a set of one inhale and its corresponding exhale phase. Hence the samples in $C_j$ can be represented as:

$$C_j = \{S_a^j, S_{a+1}^j, S_{a+2}^j, \dots S_b^j, S_{b+1}^j, S_{b+2}^j, \dots S_{b+B}^j\} \qquad (8)$$

where for all $S_i^j$:

$S_i^j := \text{in for } a \le i < b$, which constitute samples for the inhale phase, and $:= \text{in for } b \le i < b + B$, which constitute samples for the exhale phase.

At step 312 of the method (300), the breathing cycle of the subject is analyzed at the analysis module 212. The analyzing comprises (a) estimating an exhale period and an inhale period, (b) estimating a breathing rate and (c) determining a type of breathing of the subject.

At step 312A of the method (300), the exhale period and the inhale period for each breathing cycle is estimated in the inhale exhale period estimation module 214. The exhale period and the inhale period is estimated from each breathing cycle from the plurality of breathing cycles based on identification of the start of the inhale phase to the end of the exhale phase. The start of the inhale phase to the end of the exhale phase is identified based on a time stamp associated with the plurality of data samples.

In an embodiment, an inhale and an exhale period can be defined with respect to every breathing cycle $C_j$. For the breathing cycle $C_j$, a time stamp for the start of inhale phase is $$t_a^j,$$

and the time stamp for the start of exhale period is $$t_b^j.$$

Hence the inhale period and the exhale period is expressed as shown below:

$$\text{Inhale period for } C_j, I_j = t_{b-1}^j - t_a^j \qquad (9)$$

$$\text{Exhale period for } C_j, E_j = t_{b-B}^j - t_b^j \qquad (10)$$

At step 312B of the method (300), the breathing rate is estimated based on the plurality of breathing cycles at the breathing rate estimation module 216.

In an embodiment, the rate of breathing is defined as the total number of breathing cycles occurring in one minute. Hence, a real time rate of breathing can be defined with respect to every breathing cycle $C_j$ as following:

$$R_j = 60/(t_{b-B}^j - t_a^j) \qquad (11)$$

At step 312C of the method (300), the type of breathing of the subject is determined based on the plurality of parameters at the breathing type estimation module 218. The type of breathing of the subject is determined to be one of a deep/diaphragmatic breathing and a shallow/thoracic breathing.

The type of breathing is determined during the inhale phase based on the normal vector ($L_i$) and the psi angle ($\Psi_i$).

For every sample i>n, the normal vector $L_i$, as illustrated in FIG. 5A and FIG. 5B, can be estimated using Equation-6, which is perpendicular to $A_i$. Since the subject is instructed to hold the device approximately in the orientation of $L_i$ is depicted as a positive angle in FIG. 5A, while the direction of Li can either lie close to −X or +X axis depending on the type of breathing, as illustrated in FIG. 5B.

Further the psi angle ($\Psi_i$) is an angle between the $L_i$ and the positive X-axis. Further the for every sample i>n, the psi angle ($\Psi_i$) between +X axis (X=e1) and the vector $L_i$ is expressed as shown below:

$$\Psi_i = \arccos((X \odot L_i)|((X\|L_i)) \tag{12}$$

Inhalation of a deep/diaphragmatic breathing causes the lower part of the torso advance forward more with respect to the upper part, which leads to the PDA 202 being slightly rotated along +X axis as illustrated in FIG. 5A. The orientation in FIG. 5A leads to the direction of the normal vector Li to be approximately same as the +X axis. During exhalation of a deep/diaphragmatic breathing, the direction reverses and $L_i$ becomes approximately parallel to the −X axis. Inhalation of a shallow/thoracic breathing causes the upper part of the torso advance forward more with respect to the lower part, which leads to the PDA 202 being slightly rotated along −X axis as illustrated in FIG. 5A. Hence, the direction of the normal vector $L_i$ is approximately same as the −X axis. During exhalation of a shallow/thoracic breathing, the direction reverses and Li becomes approximately parallel to the +X axis as illustrated in FIG. 5B.

The type of breathing is determined during the inhale phase based on the normal vector ($L_i$) and the psi angle ($\Psi_i$), wherein the type of breathing is determined based proximity of data samples identified along the X axis based on the normal vector ($L_i$) and the psi angle ($\Psi_i$). Hence the proximity of the vector $L_i$ to +X versus-X axis can be differentiated using psi angle ($\Psi_i$), between the vector and +X axis. The proximity can be defined as follows:

$L_i$ is in proximity of $+X$ axis if and only if $\Psi_i > 90$ degrees $L_i$ is not in proximity of $+X$ axis if and only if $\Psi_i < 90$ degrees For cycle $C_j$ in reference to equation (8), let the set of inhalation samples be defined as:

$$\Omega_L^j = S_a^j, S_{a+1}^j, S_{a+2}^j, \dots, S_{b+1}^j \tag{13}$$

Further based on the psi angle ($\Psi_i$), the set of inhalation samples are further divided based on the proximity to X-axis as shown below:

$$\Omega_L^j = \{S_i^j \in \Omega^j : \Psi_i < 90\} \tag{14}$$

Wherein $$\Omega_L^j$$

is a set including all the samples where the psi angle ($\Psi_i$), between their normal and +X axis is less than 90 degrees, $$\Omega_G^j = \{S_i^j \in \Omega^j : \Psi_i > 90\} \tag{15}$$

Wherein $$\Omega_G^j$$

is a set including all the samples where the psi angle ($\Psi_i$), between their normal and +X axis is more than 90 degrees. The type of breathing is determined $$\Omega_G^j \text{ and } \Omega_L^j,$$

wherein, an overall breathing type trend for a breathing session can be established by performing a majority vote over all the breathing cycles, which is expressed as shown below:

$$C_j := \text{deep/diaphragmatic, if } n(\Omega_L^j) > n(\Omega_G^j) \tag{16}$$
$$:= \text{shallow/thoracis, if } n(\Omega_L^j) < n(\Omega_G^j)$$

Thus, the breathing analysis comprising the analyzing comprises (a) estimating an exhale period and an inhale period, (b) estimating a breathing rate and (c) determining a type of breathing of the subject is determined in the analysis module 212 and is displayed on the I/O interface(s) 106.

EXPERIMENT

Experiment has been conducted using a smartphone as a sensing device, which is lightly touched on the user's torso and the accelerometer data from accelerometer embedded in the PDA. The accelerometer data is collected and processed using the disclosed method and system to extract an inhale/exhale duration, a breathing rate and a type of breathing.

The results are illustrated using graphs of the FIGS. 6A-6C, FIGS. 7A-7C and FIGS. 8A-8C. The graphs show the dashboard showing breathing parameters in real time as the subject breathes at different rates.

Figure 6A:
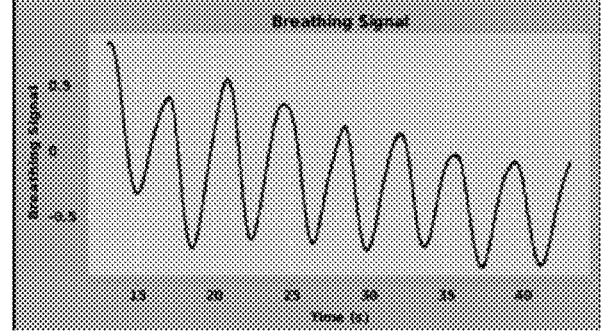
FIG. 6C illustrates real time trend of breathing signal, breathing rate, and inhale/exhale duration respectively for the case of normal breathing.
Figure 6B:
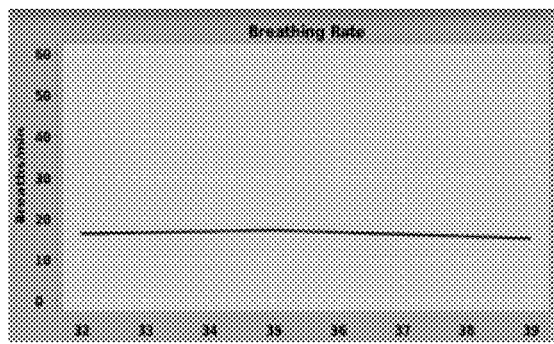
Figure 6C:
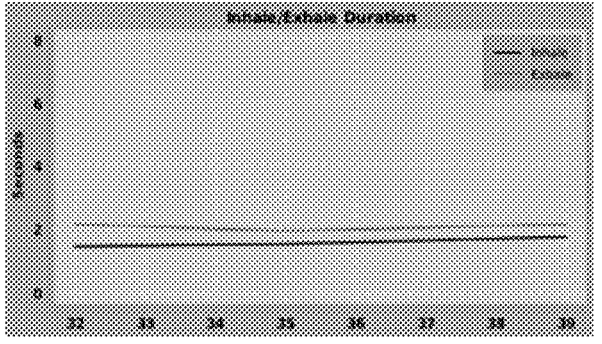

The FIG. 6A, FIG. 6B and FIG. 6C illustrates real time trend of breathing signal, breathing rate, and inhale/exhale duration respectively for the case of normal breathing. Based on the graph it can be inferred that the inhale duration is less than exhale duration, as is expected from a normal healthy breathing.

Figure 7A:
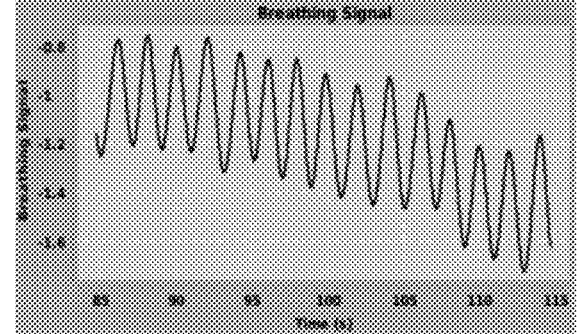
FIG. 7C illustrates real time trend of breathing signal, breathing rate, and inhale/exhale duration respectively for the case of faster breathing at approximately 30 breaths/min The FIG. 8A, FIG. 8B
Figure 7B:
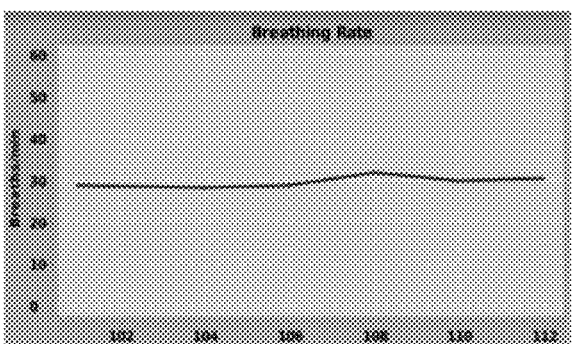
Figure 7C:
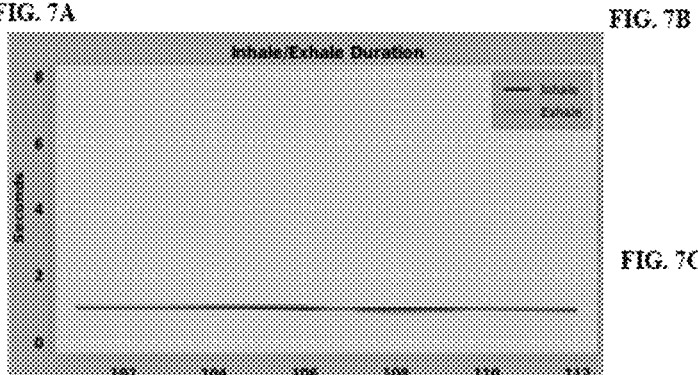

The FIG. 7A, FIG. 7B and FIG. 7C illustrates real time trend of breathing signal, breathing rate, and inhale/exhale duration respectively for the case of faster breathing at approximately 30 breaths/min ensured by clocking the breathing cycles with almost same inhale and exhale duration, equal to almost 1 second.

Figure 8A:
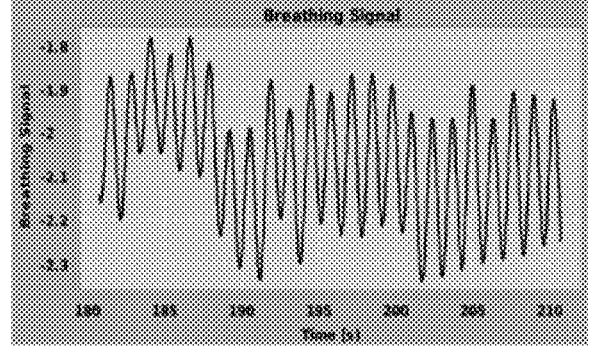
FIG. 8C illustrates real time trend of breathing signal, breathing rate, and inhale/exhale duration for the case of faster breathing at approximately 45 breaths/min.
Figure 8B:
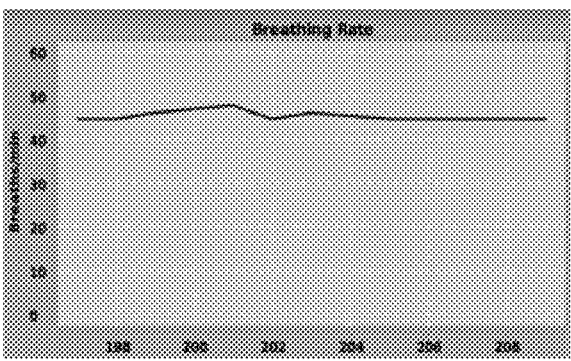
Figure 8C:
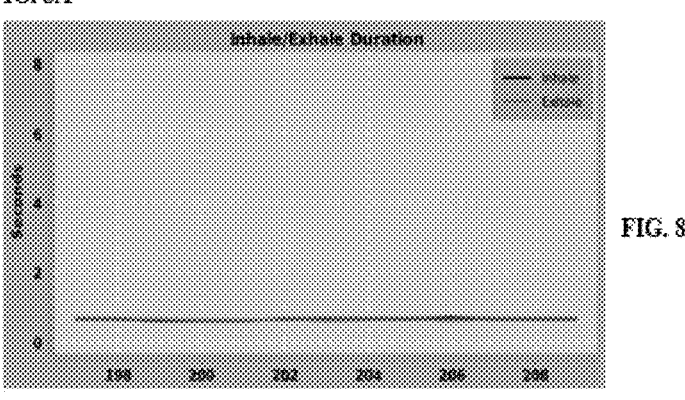

The FIG. 8A, FIG. 8B and FIG. 8C illustrates real time trend of breathing signal, breathing rate, and inhale/exhale duration for the case of faster breathing at approximately 45 breaths/min ensured by clocking the breathing cycles with almost same inhale and exhale duration, less than 1 second.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein provide a solution to address a problem of breathing analysis of a subject. Breathing analysis on a regular basis allows early detection for the onset of diseases. Early detection of diseases saves resources and cost in treatments. The existing state of art techniques mostly require specialized devices to collect-infer the breathing signal and are mostly limited to are limited to calculating breathing rate. The disclosure provides a method and a system for breathing analysis using a personal digital assistant (PDA). The breathing analysis includes (a) estimating the exhale period and the inhale period, (b) estimating the breathing rate and (c) determining the type of breathing. A PDA such as a smartphone is used receive accelerometer data from a subject. The received data is pre-processed in several steps including estimating a plurality of parameters, identifying a plurality of breathing cycles using the plurality of parameters. The breathing cycles of the subject are further analyzed at real time based on the plurality of parameters to address the problem of breathing analysis of a subject.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for real time breathing analysis of a subject using a personal digital assistant (PDA) comprising:

receiving an acceleration data of a subject, via one or more hardware processors, using the PDA, at a predefined sampling rate, wherein the PDA comprises an accelerometer, and wherein the PDA is configured to be in contact with center of torso of the subject, and with a upper half of the PDA lying over the chest and a lower half of the PDA lying over the belly of the subject with a top of the PDA directed towards the chin of the subject, wherein the acceleration data is associated with breathing of the subject and the acceleration data comprises of a plurality of data samples (i) with a time stamp;

representing the acceleration data as an acceleration vector (A), via the one or more hardware processors, based on a vectorization technique, wherein the acceleration vector (A) is represented as a three-dimensional space (X-axis, Y-axis and Z-axis) along with the time stamp and is represented as:

$$A_i = a_{x(i)}e_1 + a_{y(i)}e_2 + a_{z(i)}e_3$$

wherein, i represents one or more acceleration data samples, $a_x$, $a_y$, and $a_z$ represent acceleration in three-axes of the accelerometer at time stamp ($t_i$), and $e_1$, $e_2$ and $e_3$ represent unit vectors pointing in the X-axis, Y-axis and Z-axis respectively;

estimating a plurality of parameters from the acceleration vector using a parameter estimation technique, via the hardware processors, wherein the plurality of parameters for an acceleration data sample (i) comprises of a reference vector (R), a theta angle ($\theta_i$), a phi angle ($\varphi_i$), a normal vector ($L_i$) and a psi angle ($\Psi_i$), wherein the reference vector (R) is defined in the Y-axis and the Z-axis rotational plane of the acceleration vector (A) travels, the theta angle ($\theta_i$) is an angle between the reference vector (R) and the acceleration vector (A), the phi angle ($\varphi_i$) is an angle between the consecutive acceleration vectors, the normal vector ($L_i$) is a vector perpendicular to the plane in which the acceleration vector (A) travels and a psi angle ($\Psi_i$) is an angle between the normal vector ($L_i$) and a positive X-axis;

labelling each data sample from the plurality of data samples based on the plurality of parameters, via the one or more hardware processors, wherein the labelling comprises one of an inhale phase (in) and an exhale phase (ex), wherein the labelling is identified based on the phi angle ($\varphi_i$) of each of the data samples, where each of the data samples is labelled as the inhale phase (in) when the phi angle ($\varphi_i$) is positive and each of the data samples is labelled as the exhale phase (ex) when the phi angle ($\varphi_i$) is negative;

identifying a plurality of breathing cycles from the plurality of data samples, via the one or more hardware processors, wherein a breathing cycle from the plurality of breathing cycles is identified from a start of the inhale phase (in) to an end of the exhale phase (ex), wherein the plurality of breathing cycles are represented as a set of continuous breathing cycles C represented as a set one inhale phase and its corresponding exhale phase given by:

$$C_i = \left\{ S_a^j, S_{a+1}^j, S_{a+2}^j, \dots, S_b^j, S_{b+1}^j, S_{b+2}^j, \dots, S_{b+B}^j \right\}$$

$S_i^j$:=in for a≤i<b, which constitute samples for the inhale phase (in), and

:=in for bs i<b+B, which constitute samples for the exhale phase (ex), wherein breathing session represented as a set of continuous breathing cycles $C_j$:

$$S_F = \{C_0, C_1, C_2 \dots \}$$

where, $S_F$ is a set of breathing cycles with jth breathing cycle represented as $C_j$, $$a <= i < b,$$

wherein a, a+1, a+2 . . . constitute samples for inhale phase, b, b+1, b+2 . . . b+B constitute samples for exhale phase;

and analyzing in real time the plurality of breathing cycles of the subject, via the one or more hardware processors, by estimating an exhale period and an inhale period, estimating a breathing rate, and determining a type of breathing of the subject in a non-invasive way in real time for identifying and controlling one or more health concerns of the subject and/or early detection of one or more diseases of the subject, wherein the inhale and the exhale period is defined with respect to every breathing cycle $C_i$, the inhale period and the exhale period is expressed as:

Inhale period for $C_i$, $I_i = t_{b-1}^j - t_a^j$,

Exhale period for $C_i$, $E_i = t_{b-B}^j - t_b^j$, wherein for the breathing cycle $C_i$, a time stamp for the start of inhale phase is $$t_a^j,$$

and the time stamp for the start of exhale period is $$t_b^j,$$

wherein the analyzing process comprises:

estimating the exhale period and the inhale period for each breathing cycle among the plurality of breathing cycles based on the time stamp associated with the plurality of data samples identified for the start of the inhale phase to the end of the exhale phase;

estimating the breathing rate based on the plurality of breathing cycles, wherein the breathing rate is the total number of breathing cycles per minute, wherein a real time rate of breathing is defined with respect to the breathing cycle $C_i$ given by:

$$R_i = 60 / \left( t_{b-B}^j - t_a^j \right)$$

wherein $$t_a^j$$

is time stamp for the start of inhale phase, $$t_b^j$$

is time stamp for the start of exhale phase; and determining the type of breathing of the subject based on the plurality of parameters, wherein the type of breathing comprises one of a deep/diaphragmatic breathing and a shallow/thoracic breathing, wherein the type of breathing is determined based on proximity of data samples identified along the X-axis based on the normal vector $(L_i)$ and the psi angle $(\Psi_i)$, wherein in inhalation of a deep/diaphragmatic breathing causes the lower part of the torso advance forward more with respect to the upper part leading to the PDA rotated along the positive X-axis and the direction of the normal vector $(L_i)$ to be same as the positive X-axis, in exhalation of a deep/diaphragmatic breathing, the direction reverses and the normal vector $(L_i)$ becomes parallel to a negative X-axis, in inhalation of a shallow/thoracic breathing, the upper part of the torso advances forward with respect to the lower part of the torso, leading to the PDA rotated along the negative X-axis and the direction of the normal vector $(L_i)$ is same as the negative X-axis and in exhalation of shallow/thoracic breathing, the normal vector $(L_i)$ is parallel to the positive X-axis.

2. A system comprising:
a memory storing instructions;
one or more communication interfaces; and
one or more hardware processors coupled to the memory via the one or more communication interfaces, wherein the one or more hardware processors are configured by the instructions to:
receive an acceleration data of a subject, using a PDA, at a pre-defined sampling rate, wherein the PDA comprises an accelerometer, and wherein the PDA is configured to be in contact with center of torso of the subject, and with a upper half of the PDA lying over the chest and a lower half of the PDA lying over the belly of the subject with a top of the PDA directed towards the chin of the subject, wherein the acceleration data is associated with breathing of the subject and the acceleration data comprises of a plurality of data samples (i) with a time stamp;
represent the acceleration data as an acceleration vector (A), based on a vectorization technique, wherein the acceleration vector (A) is represented as a three-dimensional space (X-axis, Y-axis and Z-axis) along with the time stamp and is represented as:

$$A_i = a_{x(i)}e_1 + a_{y(i)}e_2 + a_{z(i)}e_3$$

wherein,
i represents one or more acceleration data samples,
$a_x$, $a_y$, and $a_z$ represent acceleration in three-axes of the accelerometer at time stamp (t), and
$e_1$, $e_2$ and $e_3$ represent unit vectors pointing in the X-axis, Y-axis and Z-axis respectively;
estimate a plurality of parameters from the acceleration vector using a parameter estimation technique, wherein the plurality of parameters for an acceleration data sample (i) comprises of a reference vector (R), a theta angle $(\theta_i)$, a phi angle $(\varphi_i)$, a normal vector $(L_i)$ and a psi angle $(\Psi_i)$, wherein the reference vector (R) is defined in the Y-axis and the Z-axis rotational plane of the acceleration vector (A) travels, the theta angle $(\theta_i)$ is an angle between the reference vector (R) and the acceleration vector (A), the phi angle $(\varphi_i)$ is an angle between the consecutive acceleration vectors, the normal vector $(L_i)$ is a vector perpendicular to the plane in which the acceleration vector (A) travels and a psi angle $(\Psi_i)$ is an angle between the normal vector $(L_i)$ and a positive X-axis;
label each data sample from the plurality of data samples based on the plurality of parameters, via the one or more hardware processors, wherein the labelling comprises one of an inhale phase (in) and an exhale phase (ex), wherein the labelling is identified based on the phi angle $(\varphi_i)$ of each of the data samples, where each of the data samples is labelled as the inhale phase (in) when the phi angle $(\varphi_i)$ is positive and each of the data samples is labelled as the exhale phase (ex) when the phi angle $(\varphi_i)$ is negative;
identify a plurality of breathing cycles from the plurality of data samples, wherein a breathing cycle from the plurality of breathing cycles is identified from a start of the inhale phase (in) to an end of the exhale phase (ex), wherein the plurality of breathing cycles are represented as a set of continuous breathing cycles $C_i$ represented as a set one inhale and its corresponding exhale phase given by:

$$C_i = \{S_a^j, S_{a+1}^j, S_{a+2}^j, \ldots, S_b^j, S_{b+1}^j, S_{b+2}^j, \ldots, S_{b+B}^j\} \text{ where for all } S_i^j:$$

$S_{:}^i := $ in for as $i < b$, which constitute samples for the inhale phase (in), and
$:= $ in for bs $i < b+B$, which constitute samples for the exhale phase (ex),
wherein breathing session represented as a set of continuous breathing cycles $C_j$:

$$S_F = \{C_0, C_1, C_2, \ldots\}$$

where, $S_F$ is a set of breathing cycles with jth breathing cycle represented as $C_j$, $$a <= i < b,$$

wherein a, a+1, a+2 . . . constitute samples for inhale phase,
b, b+1, b+2 . . . b+B constitute samples for exhale phase;
and
analyze in real time the plurality of breathing cycles of the subject, via the one or more hardware processors, by estimating an exhale period and an inhale period, estimating a breathing rate, and determining a type of breathing of the subject in a non-invasive way in real time for identifying and controlling one or more health concerns of the subject and/or early detection of one or more diseases of the subject, wherein the inhale and the exhale period is defined with respect to every breathing cycle $C_i$, the inhale period and the exhale period is expressed as:

$$\text{Inhale period for } C_i, I_i = t_{b-1}^j - t_a^j,$$

$$\text{Exhale period for } C_i, E_i = t_{b-B}^j - t_b^j,$$

wherein for the breathing cycle $C_i$, a time stamp for the start of inhale phase is $$t_a^j,$$

and the time stamp for the start of exhale period is $$t_b^j,$$

the analyzing process, wherein for the analyzing process, the one or more hardware processors are configured by the instructions to:

estimate the exhale period and the inhale period for each breathing cycle among the plurality of breathing cycles is based on the time stamp associated with the plurality of data samples identified for the start of the inhale phase to the end of the exhale phase;

estimate the breathing rate based on the plurality of breathing cycles, wherein the breathing rate is the total number of breathing cycles per minute, wherein a real time rate of breathing is defined with respect to the breathing cycle $C_i$ given by:

$$R_i = 60/\left(t_{b-B}^j - t_a^j\right)$$

wherein $$t_a^j$$

is time stamp for the start of inhale phase, $$t_b^j$$

is time stamp for the start of exhale phase; and determine the type of breathing of the subject based on the plurality of parameters, wherein the type of breathing comprises one of a deep/diaphragmatic breathing and a shallow/thoracic breathing, wherein the type of breathing is determined based on proximity of data samples identified along the X-axis based on the normal vector ($L_i$) and the psi angle ($\Psi_i$), wherein in inhalation of a deep/diaphragmatic breathing causes the lower part of the torso advance forward more with respect to the upper part leading to the PDA rotated along the positive X-axis and the direction of the normal vector ($L_i$) to be same as the positive X-axis, in exhalation of a deep/diaphragmatic breathing, the direction reverses and the normal vector ($L_i$) becomes parallel to a negative X-axis, in inhalation of a shallow/thoracic breathing, the upper part of the torso advances forward with respect to the lower part of the torso, leading to the PDA rotated along the negative X-axis and the direction of the normal vector ($L_i$) is same as the negative X-axis and in exhalation of shallow/thoracic breathing, the normal vector ($L_i$) is parallel to the positive X-axis.

3. One or more non-transitory machine-readable information storage mediums comprising one or more instructions which when executed by one or more hardware processors cause:

receive an acceleration data of a subject, using the PDA, at a pre-defined sampling rate, wherein the PDA comprises an accelerometer, and wherein the PDA is configured to be in contact with center of torso of the subject, and with a upper half of the PDA lying over the chest and a lower half of the PDA lying over the belly of the subject with a top of the PDA directed towards the chin of the subject, wherein the acceleration data is associated with breathing of the subject and the acceleration data comprises of a plurality of data samples (i) with a time stamp;

represent the acceleration data as an acceleration vector (A), based on a vectorization technique, wherein the acceleration vector (A) is represented as a three-dimensional space (X-axis, Y-axis and Z-axis) along with the time stamp and is represented as:

$$A_i = a_{x(i)} e_1 + a_{y(i)} e_2 + a_{z(i)} e_3$$

wherein, i represents one or more acceleration data samples, $a_x$, $a_y$, and $a_z$ represent acceleration in three-axes of the accelerometer at time stamp ($t_i$), and $e_1$, $e_2$ and $e_3$ represent unit vectors pointing in the X-axis, Y-axis and Z-axis respectively;

estimate a plurality of parameters from the acceleration vector using a parameter estimation technique, wherein the plurality of parameters for an acceleration data sample (i) comprises of a reference vector (R), a theta angle ($\theta_i$), a phi angle ($\varphi_i$), a normal vector ($L_i$) and a psi angle ($\Psi_i$), wherein the reference vector (R) is defined in the Y-axis and the Z-axis rotational plane of the acceleration vector (A) travels, the theta angle ($\theta_i$) is an angle between the reference vector (R) and the acceleration vector (A), the phi angle ($\varphi_i$) is an angle between the consecutive acceleration vectors, the normal vector ($L_i$) is a vector perpendicular to the plane in which the acceleration vector (A) travels and a psi angle ($\Psi_i$) is an angle between the normal vector ($L_i$) and a positive X-axis;

label each data sample from the plurality of data samples based on the plurality of parameters, via the one or more hardware processors, wherein the labelling comprises one of an inhale phase (in) and an exhale phase (ex), wherein the labelling is identified based on the phi angle ($\varphi_i$) of each of the data samples, where each of the data samples is labelled as the inhale phase (in) when the phi angle ($\varphi_i$) is positive and each of the data samples is labelled as the exhale phase (ex) when the phi angle ($\varphi_i$) is negative;

identify a plurality of breathing cycles from the plurality of data samples, wherein a breathing cycle from the plurality of breathing cycles is identified from a start of the inhale phase (in) to an end of the exhale phase (ex), wherein the plurality of breathing cycles are represented as a set of continuous breathing cycles $C_i$ represented as a set one inhale and its corresponding exhale phase given by:

$$C_i = \left\{S_a^j, S_{a+1}^j, S_{a+2}^j, \ldots, S_b^j, S_{b+1}^j, S_{b+2}^j, \ldots, S_{b+B}^j\right\} \text{ where for all } S_i^j:$$

$S_i^j$:=in for a≤i<b, which constitute samples for the inhale phase (in), and

:=in for bs i<b+B, which constitute samples for the exhale phase (ex), wherein breathing session represented as a set of continuous breathing cycles $C_j$:

$$S_F = \{C_0, C_1, C_2, \ldots\}$$

where, $S_F$ is a set of breathing cycles with jth breathing cycle represented as $C_j$, $$a \leq= i < b,$$

wherein a, a+1, a+2 . . . constitute samples for inhale phase, b, b+1, b+2 . . . b+B constitute samples for exhale phase;

and analyze in real time the plurality of breathing cycles of the subject, via the one or more hardware processors, by estimating an exhale period and an inhale period, estimating a breathing rate, and determining a type of breathing of the subject in a non-invasive way in real time for identifying and controlling one or more health concerns of the subject and/or early detection of one or more diseases of the subject, wherein the inhale and the exhale period is defined with respect to every breathing cycle $C_i$, the inhale period and the exhale period is expressed as:

$$\text{Inhale period for } C_i, I_i = t^j_{b-1} - t^j_a,$$

$$\text{Exhale period for } C_i, E_i = t^j_{b-B} - t^j_b,$$

wherein for the breathing cycle $C_i$, a time stamp for the start of inhale phase is $$t^j_a,$$

and the time stamp for the start of exhale period is $$t^j_b,$$

wherein for the analyzing process, the one or more hardware processors are configured by the instructions to:

estimate the exhale period and the inhale period for each breathing cycle among the plurality of breathing cycles is based on the time stamp associated with the plurality of data samples identified for the start of the inhale phase to the end of the exhale phase;

estimate the breathing rate based on the plurality of breathing cycles, wherein the breathing rate is the total number of breathing cycles per minute, wherein a real time rate of breathing is defined with respect to the breathing cycle $C_i$ given by:

$$R_i = 60/(t^j_{b-B} - t^j_a)$$

wherein $$t^j_a$$

is time stamp for the start of inhale phase, $$t^j_b$$

this time stamp for the start of exhale phase; and determine the type of breathing of the subject based on the plurality of parameters, wherein the type of breathing comprises one of a deep/diaphragmatic breathing and a shallow/thoracic breathing, wherein the type of breathing is determined based on proximity of data samples identified along the X-axis based on the normal vector ($L_i$) and the psi angle ($\Psi_i$), wherein in inhalation of a deep/diaphragmatic breathing causes the lower part of the torso advance forward more with respect to the upper part leading to the PDA rotated along the positive X-axis and the direction of the normal vector ($L_i$) to be same as the positive X-axis, in exhalation of a deep/diaphragmatic breathing, the direction reverses and the normal vector ($L_i$) becomes parallel to a negative X-axis, in inhalation of a shallow/thoracic breathing, the upper part of the torso advances forward with respect to the lower part of the torso, leading to the PDA rotated along the negative X-axis and the direction of the normal vector ($L_i$) is same as the negative X-axis and in exhalation of shallow/thoracic breathing, the normal vector ($L_i$) is parallel to the positive X-axis.

* * * * *